United States Patent [19]

Mundinger et al.

[11] Patent Number: 5,516,928
[45] Date of Patent: May 14, 1996

[54] PREPARAION OF 3.CYANO-3,5,5-TRIMETHYLCYCLO-HEXANONE

[75] Inventors: Klaus Mundinger, Limburgerhof; Gerhard Laqua, Mannheim; Tom Witzel, Ludwigshafen; Franz Merger, Frankenthal, all of Germany

[73] Assignee: BASF Aktiengesellschaft, Ludwigshafen, Germany

[21] Appl. No.: 395,322

[22] Filed: Feb. 28, 1995

[51] Int. Cl.$^6$ .................................................. C07C 253/10
[52] U.S. Cl. ............................................. 558/341; 558/431
[58] Field of Search ...................................... 558/341, 431

[56] References Cited

U.S. PATENT DOCUMENTS

| | | | |
|---|---|---|---|
| 5,011,968 | 4/1991 | Thunberg et al. | 558/341 |
| 5,091,554 | 2/1992 | Huthmacher et al. | 558/341 |
| 5,142,090 | 8/1992 | Pontoglio et al. | 558/341 |
| 5,179,221 | 1/1993 | Takahoso et al. | 558/341 |
| 5,183,915 | 2/1993 | Forguy et al. | 558/341 |
| 5,235,089 | 8/1993 | Woodbury et al. | 558/341 |
| 5,254,711 | 10/1993 | Pander et al. | 558/341 |

FOREIGN PATENT DOCUMENTS

| | | | |
|---|---|---|---|
| 0291074 | 11/1988 | European Pat. Off. | |
| 0502727 | 9/1992 | European Pat. Off. | |
| 0502707 | 9/1992 | European Pat. Off. | 558/341 |

OTHER PUBLICATIONS

Chemical Abstracts, vol. 105, No. 5, (1986), abstract No. 42383u, K. Kondo et al.

*Primary Examiner*—Joseph Paul Brust
*Attorney, Agent, or Firm*—John H. Shurtleff

[57] ABSTRACT

A process for the preparation of 3-cyano-3,5,5-trimethylcyclohexanone by the reaction of isophorone with hydrogen cyanide in the presence of quaternary ammonium catalysts at temperatures ranging from 80° to 180° C. and pressures ranging from 0.5 to 20 bar, in which the ammonium catalysts used are salts of the general formula I

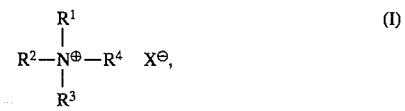

in which $R^1$, $R^2$, $R^3$, $R^4$ denote $C_1$–$C_{18}$ alkyl, $C_5$–$C_8$ cycloalkyl, aryl, $C_7$–$C_{18}$ aralkyl or $C_2$–$C_{18}$ hydroxyalkyl and X denotes $HCO_3$ or

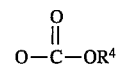

with the proviso that $R^4$ stands for $C_1$–$C_8$ alkyl when X is

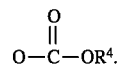

6 Claims, No Drawings

PREPARAION OF 3.CYANO-3,5,5-TRIMETHYLCYCLOHEXANONE

The present invention relates to a process for the preparation of 3-cyano-3,5,5-trimethylcyclohexanone (isophorone nitrile) by adding hydrogen cyanide to isophorone in the presence of catalytic amounts of a quaternary ammonium salt at elevated temperatures.

U.S. Pat. No. 5,011,968 describes a process for the preparation of 3-cyano-3,5,5-trimethylcyclohexanone from isophorone and hydrogen cyanide in the presence of catalytic amounts of a quaternary ammonium hydroxide or phosphonium hydroxide acting as catalyst.

EP-A 502,727 reveals on page 3 lines 10–18, that quaternary ammonium hydroxides cause, on account of their strong basicity, HCN polymerization and oligomerization of the isophorone.

U.S. Pat. No. 5,183,915 describes a process for the preparation of 3-cyano-3,5,5-trimethylcyclohexanone from isophorone and hydrogen cyanide in the presence of quaternary ammonium cyanide and phosphonium cyanide catalysts. These catalysts are, however, expensive and the 3-cyano-3,5,5-trimethylcyclohexanone yields are not totally satisfactory.

EP-A 502,707 describes the use of quaternary ammonium and phosphonium halides with the addition of a basic component. In this case, the absence of water leads to a heterogeneous reaction mixture which makes it difficult to carry out the process continuously. The presence of water on the other hand leads to an isophorone loss and necessitates elaborate purifying steps.

It was thus the object of the present invention to overcome the aforementioned drawbacks.

Accordingly, we have found a novel and improved process for the preparation of 3-cyano-3,5,5-trimethylcyclohexanone by the reaction of isophorone with hydrogen cyanide in the presence of quaternary ammonium catalysts at temperatures ranging from 80° to 180° C. and pressures ranging from 0.5 to 20 bar, wherein the ammonium catalysts used are salts of the general formula I

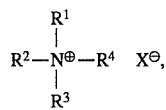
(I)

in which $R^1$, $R^2$, $R^3$, $R^4$ denote $C_1$–$C_{18}$ alkyl, $C_5$–$C_8$ cycloalkyl, aryl, $C_7$–$C_{18}$ aralkyl or $C_2$–$C_{18}$ hydroxyalkyl and X denotes $HCO_3$ or

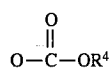

with the proviso that $R^4$ stands for $C_1$–$C_8$ alkyl when X is

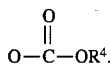

The process of the invention can be carried out as follows: For example,

A) isophorone can be placed in the reaction vessel together with the quaternary ammonium catalyst, and hydrogen cyanide can be added thereto in an inert solvent or in isophorone or B) isophorone can be placed in the reaction vessel together with hydrogen cyanide, and the quaternary ammonium catalyst can be added thereto in an inert solvent or in isophorone or C) isophorone can be placed in the reaction vessel, and hydrogen cyanide and the quaternary ammonium catalyst can be added thereto in an inert solvent or in isophorone.

The reaction mixture placed in the reaction vessel can be heated to the temperature of reaction, ie to from 80° to 180° C., preferably from 100° to 170° C. and more preferably from 120° to 140° C. The reaction pressure is usually from 0.5 to 20bar, preferably from 0.9 to 10 bar and more preferably atmospheric pressure (standard pressure). Suitable reaction vessels or reactors are, for example, stirred reactors or mixing circuits. The reaction of the invention can be carried out batchwise or, preferably, continuously, for example, by causing an amine of the general formula II $R^1R^2R^3N$ to react with a dialkyl carbonate ($R^4O$—(C=O)—$OR^4$) in the presence of isophorone and hydrogen cyanide in a stirred reactor or mixing circuit under standard pressure or under elevated pressure (from 2 to 10 bar ).

Suitable quaternary ammonium catalysts I are quaternary ammonium hydrogen carbonates (X=$HCO_3$) and preferred quaternary ammonium alkylcarbonates (X= O—(C=O)—$OR^4$) usually in amounts of from 0.005 to 5 mol %, preferably from 0.01 to 2 mol % and more preferably from 0.05 to 1 mol %, based on isophorone.

Examples of the ammonium alkylcarbonates
(X=O—(C=O)—$OR^4$) to be used as catalysts are
the following:

Tetramethylammonium methylcarbonate, methyltributylammonium methylcarbonate, tetraethylammonium methylcarbonate, benzyltrimethylammonium methylcarbonate, methyltridodecylammonium methylcarbonate, tetrabutylammonium methylcarbonate, tetrabutylammonium methylcarbonate, methyltriethylammonium methylcarbonate, phenyltrimethylammonium methylcarbonate, phenyldimethylmethylammonium methylcarbonate, tris(2-hydroxyethyl)methylammonium methylcarbonate, 2-hydroxyethyl-trimethylammonium ethylcarbonate.

Examples of suitable ammonium hydrogen carbonates (X=$HCO_3$) for use as catalysts are the following:

Tetramethylammonium hydrogen carbonate, methyltributylammonium hydrogen carbonate, tetraethylammonium hydrogen carbonate, benzyltrimethylammonium hydrogen carbonate, methyltridodecylammonium hydrogen carbonate, tetrabutylammonium hydrogen carbonate, tetrabutylammonium hydrogen carbonate, methyltriethylammonium hydrogen carbonate, phenyltrimethylammonium hydrogen carbonate, phenyldimethylmethylammonium hydrogen carbonate, tris( 2-hydroxyethyl)methylammonium hydrogen carbonate, 2-hydroxyethyl-trimethylammonium hydrogen carbonate.

The quaternary ammonium alkylcarbonates can be prepared as described in EP-A 291,074 by reaction of approximately stoichiometric amounts of tertiary amine with dialkyl carbonates. The resultant solution can be used directly without any further process step.

Using these catalysts it is possible to achieve particularly short residence times at good yields and selectivities. Oligomerization of isophorone, known to be a side-reaction, is almost completely avoided, which minimizes the distillation residues to be disposed of.

Suitable inert solvents are water and $C_1$–$C_{20}$ alkanols, preferably $C_1$–$C_8$ alkanols and more preferably $C_1$–$C_4$ alkanols such as methanol, ethanol, n-propanol, isopropanol, n-butanol, isobutanol and tert-butanol, aliphatic hydrocarbons having from 5 to 30 C-atoms, preferably having from 5 to 20 C-atoms and more preferably having with from 5 to 10 C-atoms such as n-pentane, pentane isomer mixtures, n-hexane, hexane isomer mixtures, n-heptane, heptane isomer mixtures, n-octane, octane isomer mixtures, cycloaliphatic hydrocarbons having from 5 to 20 C-atoms, preferably having from 5 to 12 C-atoms and more preferably having from 5 to 8 C-atoms such as cyclopentane, cyclohexane, cycloheptane and cyclooctane, polar solvents such as dimethylformamide, dimethylacetamide, N-methylpyrrolidone or cyclic ureas.

It is particularly preferred to use isophorone as solvent.

Neutralisation of the effluent can be effect by using acids, eg, inorganic acids such as phosphoric acid and sulfuric acid, organic acids, for example sulfonic acids such as methanesulfonic acid, toluenesulfonic acid, carboxylic acids such as formic acid, acetic acid, propionic acid, malonic acid, and adipic acid.

The substituents $R^1$, $R^2$, $R^3$, $R^4$ and X in the compounds of the general formula I have the following meanings:
$R^1$, $R^2$, $R^3$ and $R^4$ may be the same or different and denote $C_1$–$C_{18}$ alkyl, preferably $C_1$–$C_8$ alkyl such as methyl, ethyl, n-propyl, isopropyl, n-butyl, isobutyl, sec-butyl, tert-butyl, n-pentyl, isopentyl, sec-pentyl, neo-pentyl, 1,2-dimethylpropyl, n-hexyl, isohexyl, sec-hexyl, n-heptyl, isoheptyl, n-octyl, isooctyl and more preferably $C_1$–$C_4$alkyl such as methyl, ethyl, n-propyl, isopropyl, n-butyl, isobutyl, sec-butyl and tert-butyl, $C_5$–$C_8$ cycloalkyl, preferably cyclopentyl, cyclohexyl and cyclooctyl and more preferably cyclopentyl and cyclohexyl, aryl such as phenyl, 1-naphthyl and 2-naphthyl, preferably phenyl, $C_7$–$C_{18}$ aralkyl, preferably $C_7$–$C_{12}$ phenylalkyl such as benzyl, 1-phenethyl, 2-phenethyl, 1-phenylpropyl, 2-phenylpropyl, 3-phenyl-propyl, 1-phenylbutyl, 2-phenylbutyl, 3-phenylbutyl and 4-phenylbutyl and more preferably benzyl, 1-phenethyl and 2-phenethyl, $C_2$–$C_{18}$ hydroxyalkyl, preferably $C_2$–$C_{10}$ hydroxyalkyl and more preferably $C_2$–$C_5$ hydroxyalkyl such as 1-hydroyethyl, 2-hydroxyethyl, 1-hydroy-n-propyl, 2-hydroxy-n-propyl, 3-hydroxy-n-propyl, X denotes $HCO_3$ or

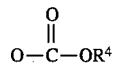

with the proviso that $R^4$ stands for $C_1$–$C_8$ alkyl, preferably for $C_1$–$C_4$ alkyl and more preferably for methyl or ethyl when X is

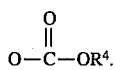

3-cyano-3,5,5-trimethylcyclohexanone (isophorone nitrile) is an intermediate for the preparation of isophorone diamine, which is used as an epoxy setting agent or as a monomer for polyamines and polyurethanes.

EXAMPLES

Example 1

In reaction apparatus equipped with a stirrer, condenser, thermometer and dripping funnel there are placed 622 g (4.5 mol) of isophorone and 4.47 g (30 mmol) of tetramethylammonium methylcarbonate. Over a period of 60 min there are added, at 120° C., 288.3 g of a mixture of isophorone and hydrocyanic acid (3 mol of HCN, 1.5mol Of isophorone). When all of said mixture has been added, the HCN concentration is 20 ppm. 3.5g of 85% strength $H_3PO_4$ are then added and the mixture is distilled at 0.1 mbar. There are obtained 426.6g of isophorone (99% based on converted isophorone) and 476.8 g of 3-cyano-3,5,5-trimethylcyclohexanone (96.2% based on HCN used).

Example 2

To 622 g (4.5 mol) of isophorone in the presence of 4.14 g (0.02mol) of butyltrimethylammonium methylcarbonate there are added 288.3 g of a mixture of 3 mol of HCN and 1.5 mol of isophorone over a period of 120 min and at a temperature of 115° C. Following neutralization with 4 g of $H_3PO_4$ the mixture is distilled. There are obtained 424.3 g of isophorone and 478.3 g of 3-cyano-3,5,5-trimethylcyclohexanone. This is equivalent to a yield of 98.8% based on converted isophorone and 96.5% based on HCN used.

Example 3

To a two-stage cascade of stirred boilers each having a capacity of 250 mL there are fed, at a temperature of 120° C., 102.9 g of isophorone, 10.06 g anhydrous hydrogen cyanide containing stabilizer and 0.72 g of a 50% strength methanolic tetramethylammonium methylcarbonate solution, per hour. The content of HCN at the outlet of the 2nd reactor is 100 ppm. To the reaction mixture there is the added 0.25 g of 85 % strength $H_3PO_4$ per hour and the mixture is collected in a receiver. Following a first-run time of 24 h, 620 g of the stabilized crude mixture are passed on to a fractional distillation stage. Following the separation of 2.2 g of low-boiling compounds there are removed by distillation, under a reduced pressure of I mbar, 286.1 g of isophorone having a boiling point of 40° to 42° C. and 324.9 g of 3 -cyano-3,5,5-trimethylcyclohexanone having a boiling point of 94° to 95° C., which is equivalent to a yield of 96.8% based hydrogen cyanide used and 98.8% based on converted isophorone.

The distillation residues weigh 6.9 g, which is equivalent to 1.2% based on the crude product used.

Example 4

To 622 g (4.5 mol) of isophorone there are added, at 120° C. over a period of 120min, a mixture of 207.3 g (1.5mol) of isophorone and 81 g (3.0 mol) of HCN in the presence of 5.2 g (0.02 mol) of a 50% strength aqueous tetramethylammonium methylcarbonate solution. 10 min after the end of the metering operation the HCN concentration is only 140 ppm. Following neutralization with 4 g of $H_3PO_4$ the mixture is distilled. Following a first runoff of 3 g, there are obtained 422.6 g of isophorone and 476.7 g of 3-cyano-3, 5,5-trimethylcyclohexanone. This is equivalent to a yield of 96.2% based on HCN used and 98% based on isophorone converted.

Example 5

To 622 g (4.5 mol) of isophorone in the presence of 4 g (0.021 mol) of triethylmethylammonium methylcarbonate there are added 288.3 g of a mixture of 3 mol of HCN and 1.5 mol of isophorone, over a period of 120 min and at a reaction temperature of 120° C. The HCN conversion at the end of the reaction is 99.9%. Following neutralization with 2.4g of H₃PO₄ the mixture is distilled. There are obtained 424.1 g of isophorone and 479.2 g of 3-cyano-3,5,5-trimethylcyclohexanone: the distillation residues weigh 12.8 g, this is equivalent to 1.4% based on the crude product used. The 3-cyano-3,5,5-trimethylcyclohexanone yield is thus 96.7% and the isophorone selectivity 99%.

Comparative Example

To 415 g (3 mol) of isophorone containing 12 g (0.077 mol) of tetraethylammonium cyanide there are added dropwise, over a period of 1 hour, 81 g (3 mol) of hydrogen cyanide at a reaction temperature of 108° C. Following a post-reacting period of 3 min the HCN concentration is 0.16%. The effluent is neutralized with 9 g of H₃PO₄ and distilled. There are obtained 15 g of isophorone and 443.6 g of 3-cyano-3,5,5-trimethylcyclohexanone. This is equivalent to a yield of 89.6% based on HCN used and 93% based on converted isophorone. The distillation residues weigh 28.2 g, which is equivalent to 5.5% based on crude product used.

We claim:

1. A process for the preparation of 3-cyano-3,5,5-trimethylcyclohexanone by the reaction of isophorone with hydrogen cyanide in the presence of a quaternary ammonium catalyst at temperatures ranging from 80° to 180° C. and pressures ranging from 0.5 to 20 bar, wherein the ammonium catalyst used is a salt of the general formula I

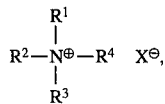

in which

R¹, R², R³, R⁴ denote C₁–C₁₈ alkyl, C₅–C₈ cycloalkyl, aryl, C₇–C₁₈ aralkyl or C₂–C₁₈ hydroxyalkyl and X denotes HCO₃ or

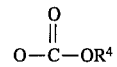

with the proviso that R⁴ stands for C₁–C₈ alkyl when X is

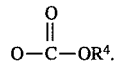

2. A process for the preparation of 3-cyano-3,5,5-trimethylcyclohexanone as defined in claim 1, wherein the reaction is carried out in the presence of from 0.005 to 5 mol % of an ammonium catalyst of the formula I.

3. A process for the preparation of 3-cyano-3,5,5-trimethylcyclohexanone as defined in claim 1, wherein the reaction is carried out at temperatures of from 10° to 170° C.

4. A process for the preparation of 3-cyano-3,5,5-trimethylcyclohexanone as defined in claim 1, wherein the reaction is carried out at pressures of from 0.9 to 10 bar.

5. A process for the preparation of 3-cyano-3,5,5-trimethylcyclohexanone as defined in claim 1, wherein the reaction is carried out at atmospheric pressure.

6. A process as claimed in claim 1, wherein the reaction is carried out continuously.

* * * * *

UNITED STATES PATENT AND TRADEMARK OFFICE
CERTIFICATE OF CORRECTION

PATENT NO. : 5,516,928
DATED : May 14, 1996
INVENTOR(S) : Klaus Mundinger, Gerhard Laqua, Tom Witzel, Franz Merger It is certified that error appears in the above-indentified patent and that said Letters Patent is hereby corrected as shown below:

On the title page: Item [54]

-- PREPARATION OF 3-CYANO-3,5,5-TRIMETHYLCYCLOHEXANONE --

In column 1, line 14, change "EP-A 502,727" to read
-- EP-A 502,707 --

Signed and Sealed this

Fifteenth Day of October, 1996

Attest:

BRUCE LEHMAN

*Attesting Officer*    Commissioner of Patents and Trademarks